(12) United States Patent
Muderlak et al.

(10) Patent No.: US 9,562,721 B2
(45) Date of Patent: Feb. 7, 2017

(54) THROUGH SURFACE HAND DRYING SYSTEM

(71) Applicant: Xela Innovations, LLC, Glendale, WI (US)

(72) Inventors: Todd J. Muderlak, Whitefish Bay, WI (US); Kenneth J. Muderlak, Milwaukee, WI (US)

(73) Assignee: Xela Innovations, LLC, Glendale, WI (US)

( * ) Notice: Subject to any disclaimer, the term of this patent is extended or adjusted under 35 U.S.C. 154(b) by 712 days.

(21) Appl. No.: 13/842,603

(22) Filed: Mar. 15, 2013

(65) Prior Publication Data

US 2014/0259735 A1 Sep. 18, 2014

(51) Int. Cl.
*F26B 3/00* (2006.01)
*F26B 20/00* (2006.01)
*A47K 10/48* (2006.01)

(52) U.S. Cl.
CPC ............... *F26B 20/00* (2013.01); *A47K 10/48* (2013.01)

(58) Field of Classification Search
CPC ............................ A47K 2210/00; A47K 10/48
USPC ......... 34/486, 443, 572; 4/623; 222/52, 129, 222/132, 135, 192
See application file for complete search history.

(56) References Cited

U.S. PATENT DOCUMENTS

| | | | |
|---|---|---|---|
| 1,494,883 A | 5/1924 | Bassette et al. | |
| 2,281,370 A | 4/1942 | Morrison et al. | |
| 4,336,619 A | 6/1982 | Hinkel et al. | |
| 5,765,242 A | 6/1998 | Marciano | |
| 7,107,631 B2 | 9/2006 | Lang et al. | |
| 7,228,874 B2 | 6/2007 | Bolderheij et al. | |
| 7,555,209 B2 | 6/2009 | Pradas Diez et al. | |
| 2001/0030243 A1* | 10/2001 | Hurry et al. | 239/60 |
| 2002/0185500 A1* | 12/2002 | Muderlak et al. | 222/1 |
| 2005/0076529 A1* | 4/2005 | Holmes | 34/90 |
| 2008/0279729 A1* | 11/2008 | Chen | 422/123 |
| 2009/0077736 A1* | 3/2009 | Loberger | E03C 1/057 4/623 |
| 2012/0291195 A1 | 11/2012 | Courtney et al. | |
| 2013/0086741 A1* | 4/2013 | Bayley et al. | 4/623 |

FOREIGN PATENT DOCUMENTS

| | | |
|---|---|---|
| CN | 201198587 Y | 2/2009 |
| EP | 679358 A2 | 11/1995 |
| JP | S5692581 | 7/1981 |

(Continued)

OTHER PUBLICATIONS

International Search Report and Written Opinion for international application No. PCT/US2014/025920, date of mailing Oct. 13, 2014, 16 pages.

(Continued)

*Primary Examiner* — Kenneth Rinehart
*Assistant Examiner* — John McCormack
(74) *Attorney, Agent, or Firm* — Husch Blackwell LLP

(57) ABSTRACT

The present disclosure provides an apparatus for automatically dispensing air, for example, for hand drying, through either a dedicated air only spout (side mount embodiment) or through a multi-use spout configured for dispensing water, soap and/or air. The air drying module, which is typically positioned below a counter, can be modified according to the system needs to operate with hot and/or cold air and to optionally include a filter and/or fragrance dispenser.

20 Claims, 19 Drawing Sheets

(56) References Cited

FOREIGN PATENT DOCUMENTS

| | | | |
|---|---|---|---|
| JP | 01236025 A | | 9/1989 |
| JP | H0327796 | | 3/1991 |
| JP | 04215727 A | | 8/1992 |
| JP | 2000262433 A | | 9/2000 |
| JP | 2000271039 A | | 10/2000 |
| JP | 2001140305 A | * | 5/2001 |
| JP | 2002115303 A | | 4/2002 |
| JP | 2003275112 A | | 9/2003 |
| JP | 2006192250 | | 7/2006 |
| JP | 2006255225 A | | 9/2006 |
| JP | 2006304926 A | | 11/2006 |
| JP | 2007209459 A | | 8/2007 |
| JP | 2007296147 A | | 11/2007 |
| JP | 2009088657 A | | 4/2009 |
| WO | 2007015036 | | 2/2007 |
| WO | 2009062546 A1 | | 5/2009 |

OTHER PUBLICATIONS

Home Chunk; http://www.homechunk.com/6149/2012/12/04/airblade-maker-dyson-patents-a-faucet-that-double . . . ; printed Mar. 13, 2014, 3 pages.

* cited by examiner

THROUGH SURFACE HAND DRYING SYSTEM

FIELD

Embodiments of this disclosure relate to an automatic dispenser apparatus for dispensing a flow of air and/or water.

BACKGROUND

In washrooms and other locations, wall-mounted hand dryers that are hands-free and automatically activated, are typically installed for users to dry their hands. However, a drawback of wall-mounted dryers is that a person who has washed their hands in a sink is required to move to the location of the dryer, resulting in water dripping from their hands onto the sink counter or floor.

More recently, high speed, automatic drying changes for inserting the user's hands have been installed into many washrooms. However, such devices are very cumbersome and extremely noisy, particularly in an enclosed space such as a washroom.

It would be desirable to provide a hand drying apparatus and set-up that overcomes such drawbacks and can be readily installed into an existing washroom or other set-up.

SUMMARY

Embodiments of the present disclosure provide a dispenser apparatus for dispensing air, for example, for drying hands. The air dispensing apparatus can be mounted, for example, on a sink, counter, table, cabinet or other support substrate. The system allows for hand drying either through a dedicated air only spout (side mount embodiment) or through a multi-use spout (water, soap and/or air). The air drying module, which is typically positioned below the counter, can be modified according to the system to operate with hot and/or cold air and to include filters and/or fragrance dispensing options.

The air dispensing apparatus of the disclosure provides a robust automatic hand drying apparatus that can be affixed beneath a counter, table, etc. to either a dedicated spout (air only) or to a spout that is configured to dispense soap, water, sanitizer and/or other fluid. The apparatus can be configured to include air filtering to remove impurities from the air used to dry hands. The apparatus can also be configured to dispense an air fragrance that is separate from the air used to dry the user's hands by leveraging the motor/power and associated air movement created to better disperse fragrance into the environment. The air dispensing module is very serviceable, with the air drying module being easily removed from the assembly.

In embodiments, the disclosure provides an apparatus for automatically dispensing air, comprising a spout assembly mounted through a support substrate and connected to a drying module comprising a housing. In embodiments, the spout assembly is structured with an outlet for dispensing the air therethrough, an infrared sensor, and one or more indicator lights. The housing of the drying module contains a motor-driven fan operable for forcing airflow through the outlet of the spout assembly, and an air intake vent. Activation of the infrared sensor activates the drying module to draw air into the drying module and force the air through the outlet of the spout assembly.

The drying module of the air dispensing apparatus can optionally include an air heating mechanism, an air filter and/or a fragrance module that can be releasably mounted to the drying module and can be configured to release a fragrance into the surrounding air. In embodiments, the spout assembly and the drying module are connected by a quick release mechanism, e.g., a bayonet mount, to provide easy connection and disconnection.

In embodiments, the air dispensing apparatus is mounted adjacent to an automatic faucet, and the apparatus and the faucet are connected through a processor to coordinate activation of water and air delivery. In embodiments, the air dispensing apparatus comprises a processor electrically connected to a water intake for the faucet and is configured such that the apparatus is not activated during water flow to the faucet. In another embodiment, a valve mechanism is connected to a water intake pipe for the faucet and electrically connected to a processor for the air dispensing apparatus, which is configured to activate the valve mechanism to stop water flow to the faucet when the apparatus is activated.

In another embodiment, the disclosure provides an apparatus for automatically dispensing air and water as a multi-functional apparatus, comprising a spout assembly mounted through a support substrate and connected to a water source dispenser and to a drying module. The spout assembly is structured with an outlet for dispensing the water and the air therethrough, an infrared sensor and, optionally, one or more indicator lights.

In embodiments of the multi-functional air dispensing apparatus, activation of the infrared sensor activates a microprocessor configured to first activate the water source dispenser for a first time period to dispense water through the outlet of the spout assembly, then secondly activate the drying module to draw air into the drying module and force the air through the outlet of the spout assembly for a second time period. In another embodiment, first and second infrared sensors can be positioned on either side of the spout assembly, wherein activation of the first sensor actuates water flow and activation of the second sensor actuates air flow. In embodiments, the infrared sensor is programmed through a processor to dispense water by a single pass of an object, and dispense air by two or more passes of an object within a set time period.

The design of the air dispensing apparatus allows for either a new installment or an easy retrofit with an automatic (or manual) faucet, with a connection from a processor to an automatic faucet to control the timing and/or duration of water flow and air flow. In other embodiments, a retrofit with an existing manual or automatic faucet can be easily achieved through connections from the air dispensing apparatus to the water intake for the faucet and/or a water shut-off valve.

BRIEF DESCRIPTION OF THE DRAWINGS

Preferred embodiments of the disclosure are described below with reference to the following accompanying drawings, which are for illustrative purposes only. Throughout the following views, the reference numerals will be used in the drawings, and the same reference numerals will be used throughout the several views and in the description to indicate the same or like parts.

DETAILED DESCRIPTION

Embodiments of the disclosure relate to an apparatus for automatically dispensing a flow of air. The air dispensing apparatus can be mounted on a sink, a counter, a table, a cabinet or other substrate and provides the ability to dispense air automatically to the user The air dispensing apparatus can be automatically activated using an infrared or similar sensor and an associated drive system.

Figure 1:
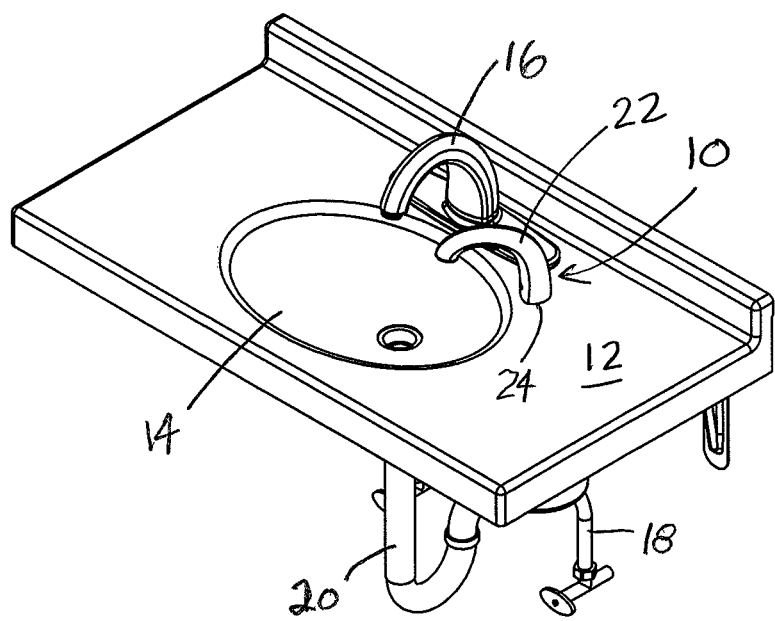
FIG. 1 is a perspective view of an embodiment of an air dispensing apparatus according to the disclosure mounted on the counter of a sink.
Figure 2:
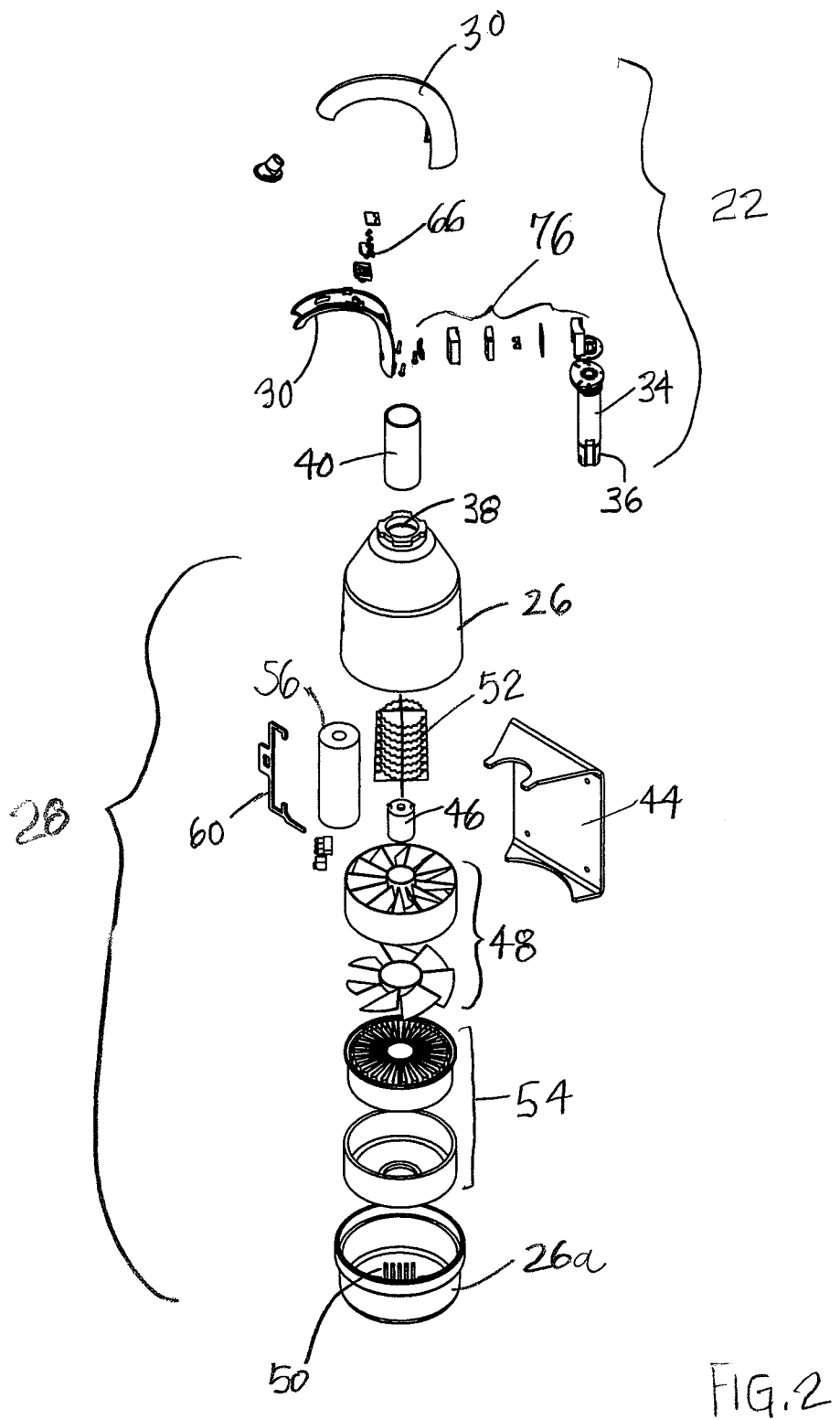
FIG. 2 is an exploded view of the air dispensing apparatus of FIG. 1.
Figure 3:
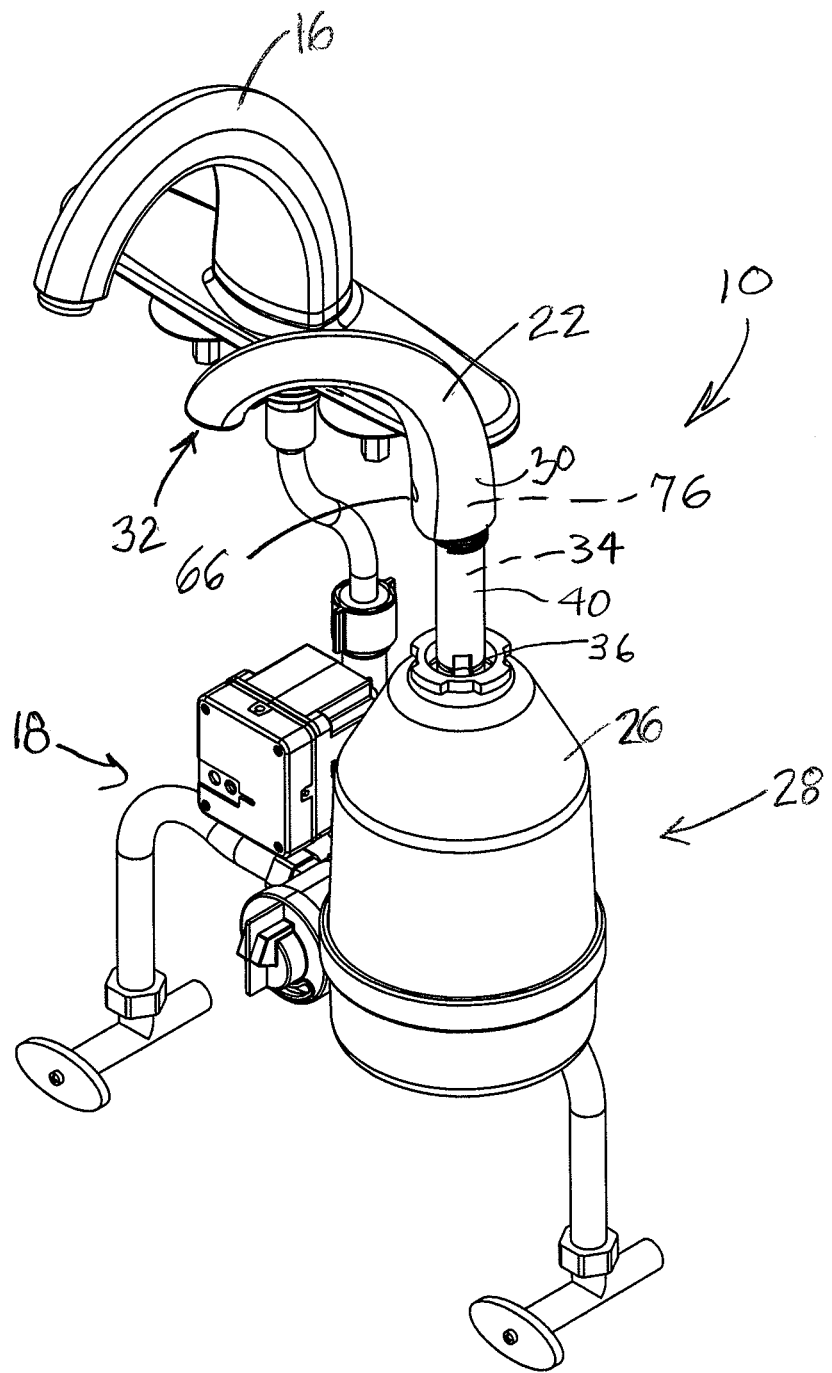
FIG. 3 is a perspective view of the air dispensing apparatus as depicted in FIG. 1, with the sink and counter not depicted.
Figure 4:
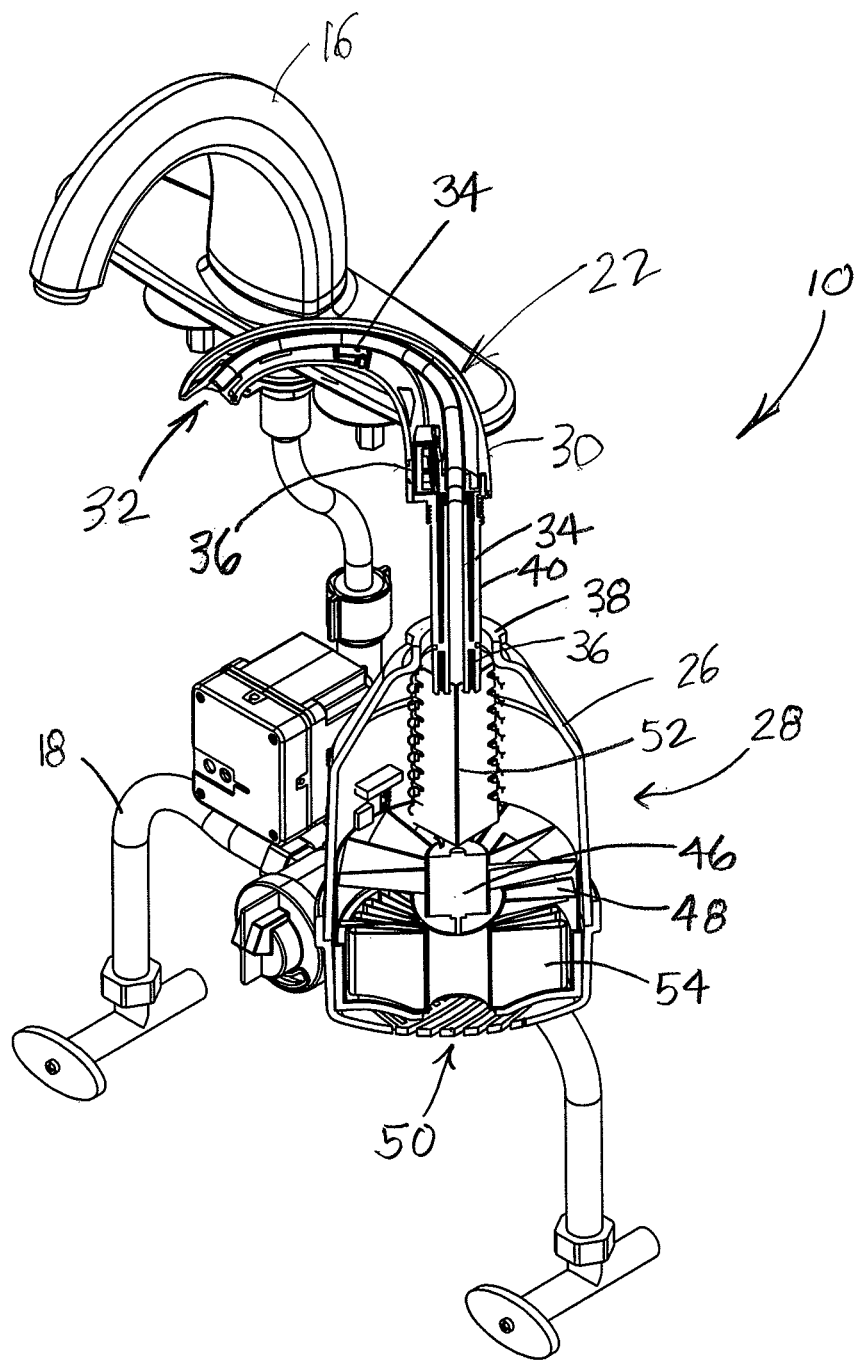
FIG. 4 is a perspective, partial cross-sectional view of the air dispensing apparatus of FIG. 3.

An embodiment of an air dispensing apparatus 10 according to the disclosure is described with reference to FIGS. 1-6. Referring to FIG. 1, in the depicted embodiment, the air dispensing apparatus 10 is shown mounted through a counter 12 of a sink 14 as a side mount adjacent to a water faucet 16. Also depicted are a water valve and mixer assembly 18 for automatic hot and cold water delivery to the water faucet 16, and a standard plumbing drain 20 connected to the sink 14. FIG. 2 illustrates the apparatus 10 in an exploded view, and FIGS. 3-4 depict the air dispensing apparatus 10 positioned adjacent to a water faucet 16 without the presence of the counter 12 or sink 14.

As shown in FIG. 1, the air dispensing apparatus 10 comprises a spout assembly 22 mounted through a hole 24 in the counter 12 (or other support substrate). The spout assembly 22 is releasably connected to the housing 26 of a drying module 28, which are positioned under the counter 12. As a power source, the drying module 28 can be, for example, hard-wired to a power source, powered by a power pack leveraging batteries, or other means known and used in the art.

The spout assembly 22 is structured with spout housing 30 with an outlet 32 for dispensing the air therethrough and a stem section 34 having an end 36 that is structured for mating connection onto the open end 38 of the drying module housing 26. As depicted in FIGS. 2-4, in embodiments, the ends 36, 38 of the stem section 34 and the drying module housing 26 are connected by a quick release mechanism, for example, by a bayonet mount. As illustrated, the stem section 34 of the spout assembly 22 can be housed within a tubular protective sleeve 40. In embodiments, the spout assembly 22 and the drying module housing 26 can be connected by a flexible tubing 42 (as depicted, for example, in FIG. 18) with the drying module 28 affixed to a support bracket 44 that can be mounted on a supporting wall or other substrate.

The housing 26 of the drying module 28 contains a motor 46 connected to a fan assembly 48 that is operable for forcing airflow through the outlet 32 of the spout assembly 22. The drying module housing 26 further includes an air intake vent 50 at the bottom section 26a of the housing 26.

In embodiments, the housing 26 can contain an optional air heating mechanism 52, e.g., heater coils, to warm the air as it passes through the drying module 28. The drying module 28 can further include an air filter 54 for filtering the intake air before it is dispensed from the apparatus.

Referring now to FIG. 2 and FIGS. 7-10, in embodiments, the housing 26 of the drying module 28 can comprise a fragrance dispersing mechanism. In some embodiments, the apparatus 10 can include a module 56 comprising a fragrance dispersing mechanism that can be releasably mounted in an external structure 58 of the drying module housing 26. The fragrance dispersing module 56 can be constructed of a fragranced material or structured to contain a fragranced material, for example, a wicking material containing a fragrance substance, a fragrance block or gel, etc.

In embodiments, the wicking material is composed of an absorbent material. Nonlimiting examples of suitable materials include polymeric materials, cellulosic-based materials, fabrics, polyesters, polyolefins, nylon, cellulosics, acetates, foams (hydrophilic polyurethane), polyolefins, polyamides, acrylics, styrenics, among other materials.

The fragrance dispersing module 56 can be connected to the drying module housing 26 such that, upon activation of the drying module 28, air will flow (one way) through vents from the drying module 28 into the fragrance dispersing module 56, such that the fragrance is dispersed into the air outside the drying module 28 but does not pass into the spout assembly 22. The fragrance dispersing module 56 can include a handle 60 for ease of removal and placement. In embodiments, the drying module 28 and/or the fragrance dispersing module 56 can be configured with a mechanism (not shown) to control the incoming air flow from the drying module 28 into the fragrance dispersing module 56.

Figure 5:
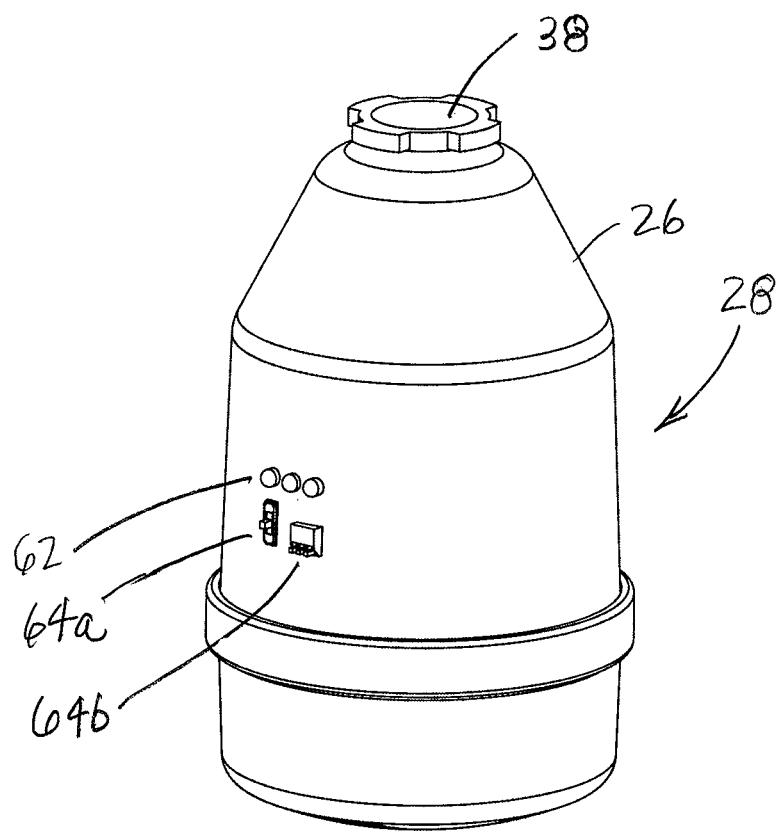
FIG. 5 is a perspective view of the air drying module of the air dispensing apparatus of FIG. 4.
Figure 6:
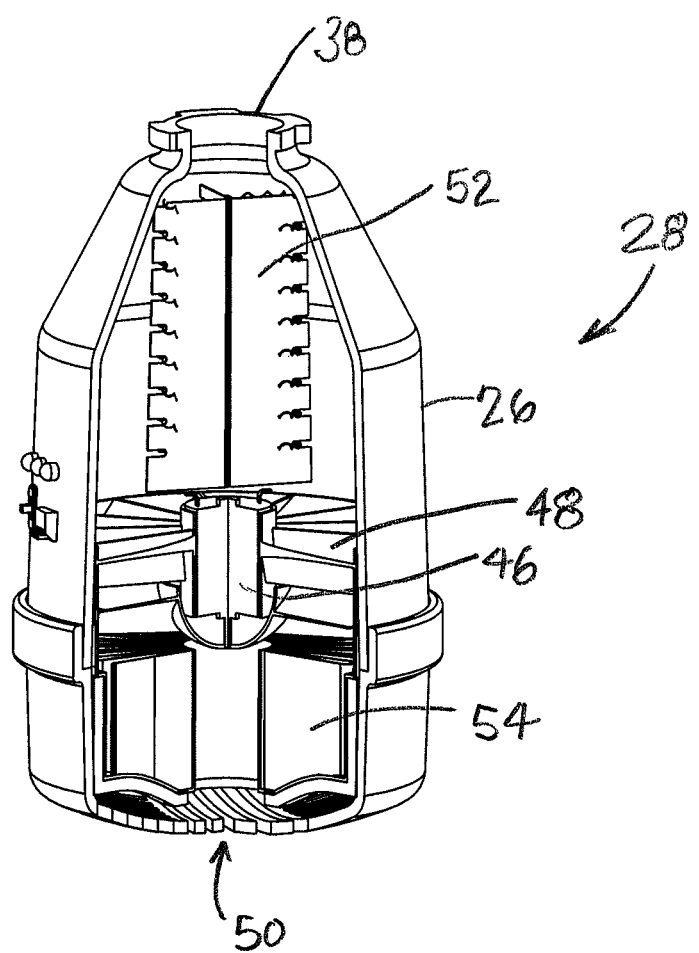
FIG. 6 is an elevational, partial cross-sectional view of the air drying module of FIG. 5.
Figure 7:
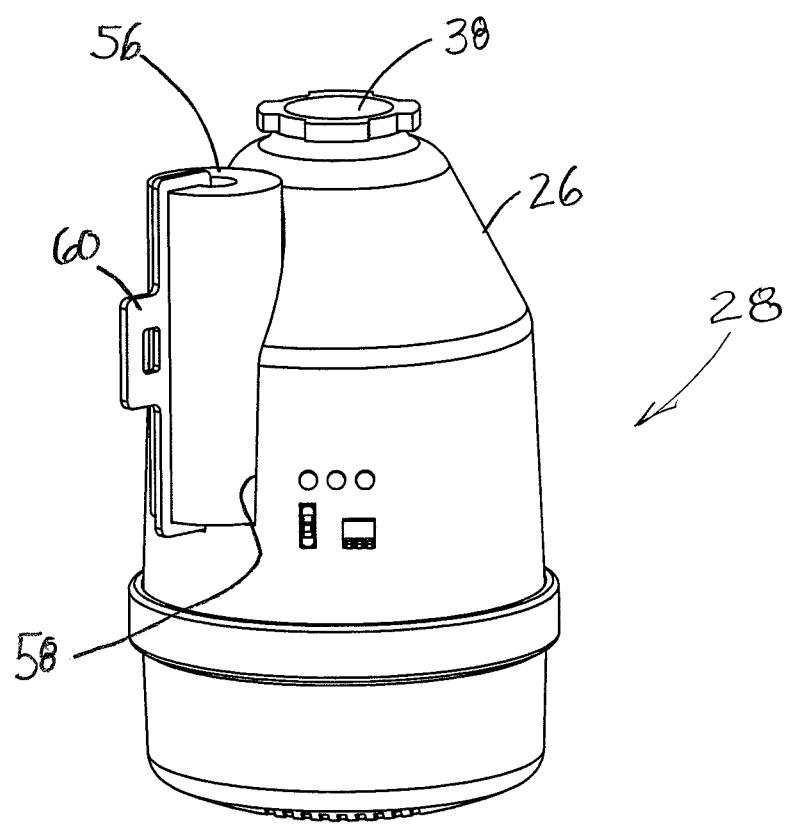
FIG. 7 is an embodiment of an air drying module with a fragrance dispersing module mounted thereon.
Figure 8:
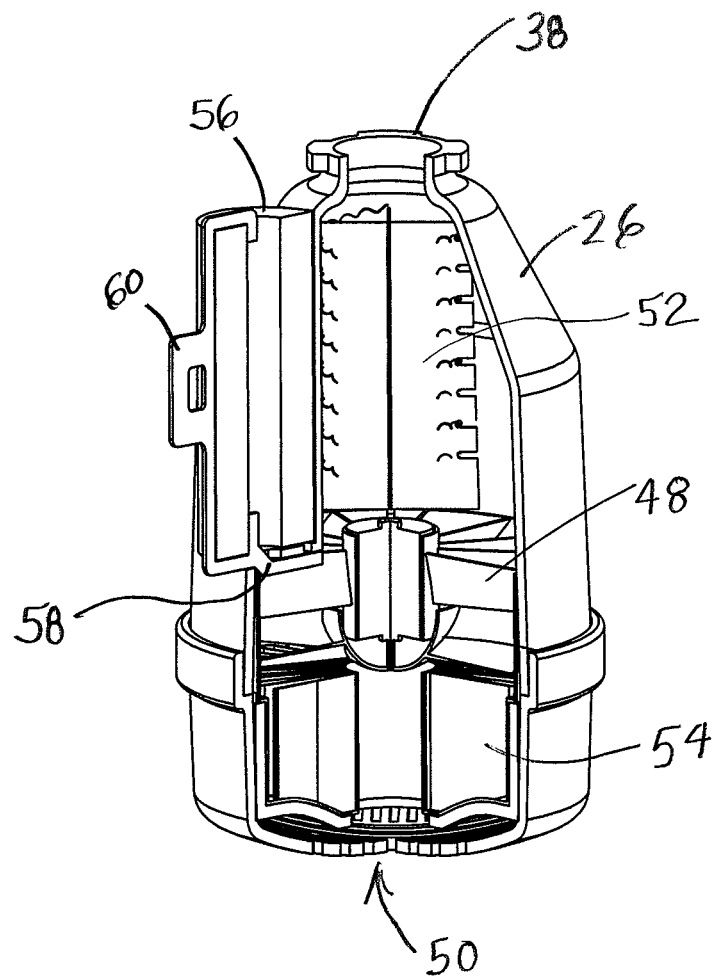
FIG. 8 is an elevational, partial cross-sectional view of the air drying module of FIG. 7.
Figure 9:
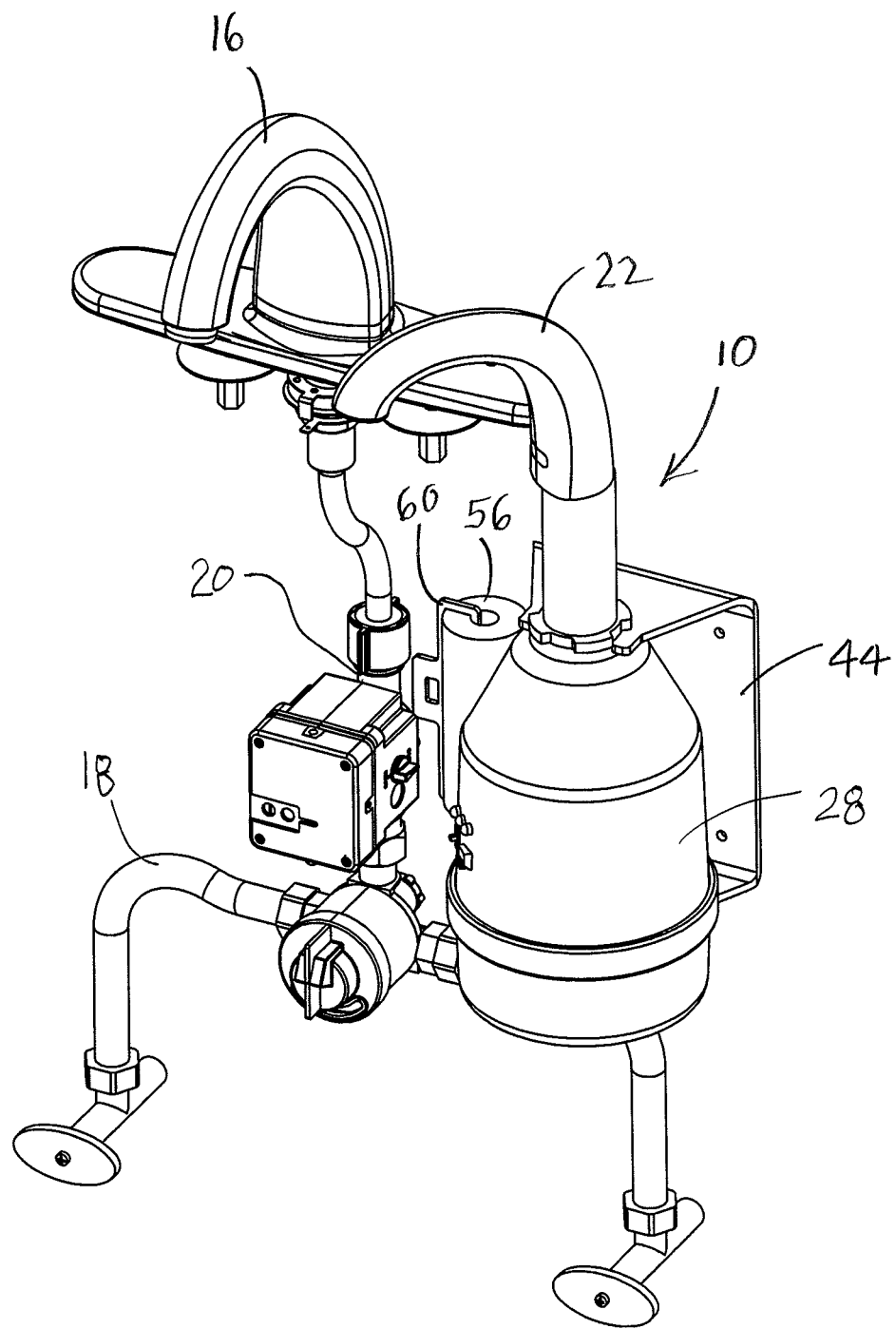
FIG. 9 is a perspective view of another embodiment of an air dispensing apparatus according to the disclosure mounted adjacent to a faucet, with the air drying module depicted in FIG. 7.
Figure 10:
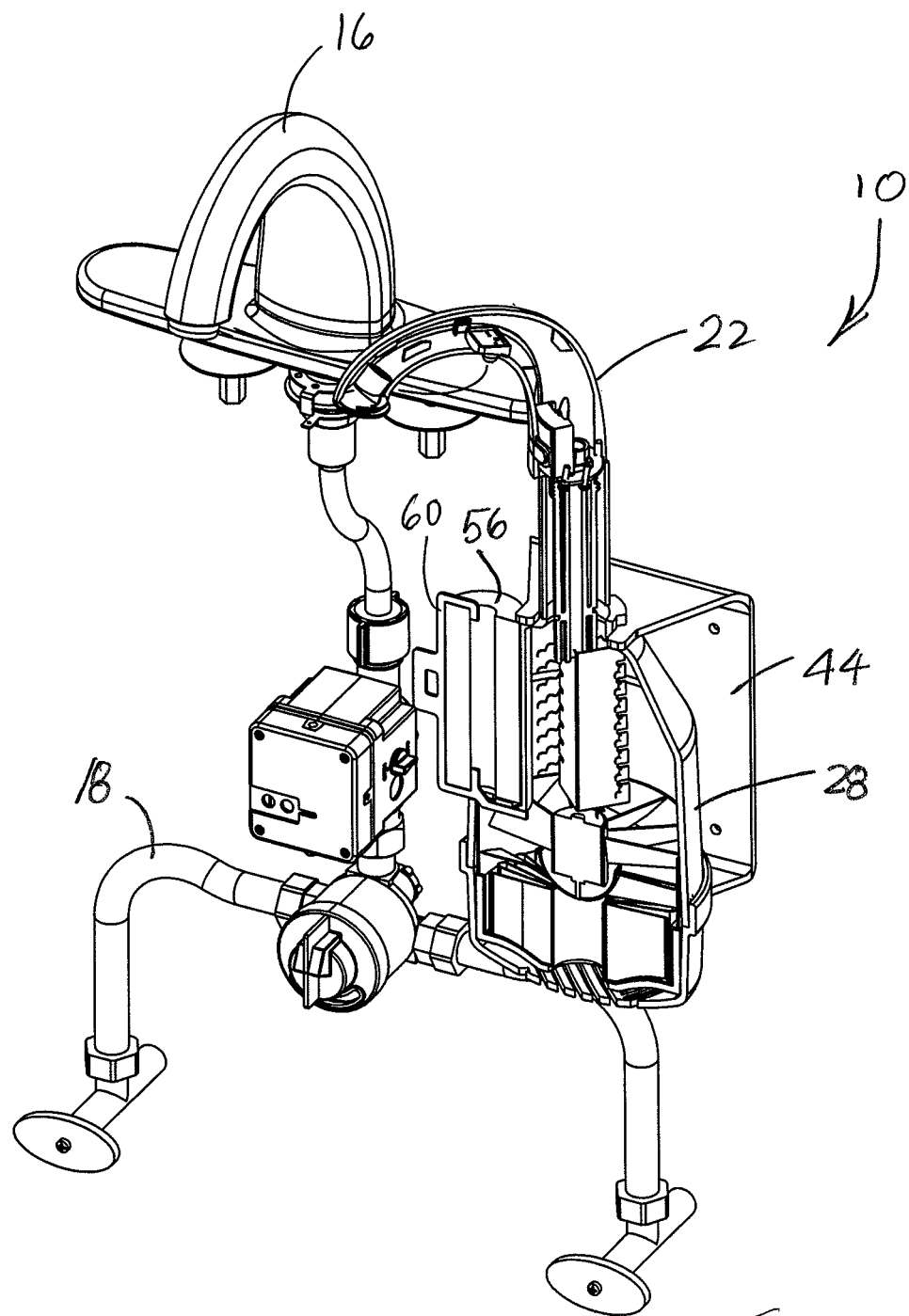
FIG. 10 is a perspective, partial cross-sectional view of the air dispensing apparatus of FIG. 9.

As illustrated in FIG. 5, the drying module 28 can includes one or more LED indicator lights 62 and/or control switches 64a, 64b. In embodiments, the drying module 28 is structured with a plurality of LED indicator lights 62 in an array and optionally colored, for example, to indicate power, filter replacement, unit working without heat, replacement of fragrance dispersing module, system malfunction, etc. In embodiments, the drying module 28 can include an on/off switch or a slider switch 64*a* (e.g., to turn on/off the air heating mechanism 52 and/or a dip switch 64*b* to control unit settings such as timing of air flow, system activation, etc.

As illustrated in FIG. 3, an infrared sensor 66 is situated in the spout assembly 22 to optimize 'object in view' performance and minimize accidental triggering of air flow. Activation of the infrared sensor 66 activates the drying module 28 to draw air into the drying module and force the air through the outlet 32 of the spout assembly 22.

The infrared sensor 66 is connected to a processor (PCB) 76 within the spout assembly, which, in turn, is connected to a power source. The processor 76 is configured to communicate with the sensor 66 and the fan motor 46 via wiring to turn on and off the fan motor 46 of the drying module 28 when the infrared sensor 66 is or isn't activated.

Figure 11:
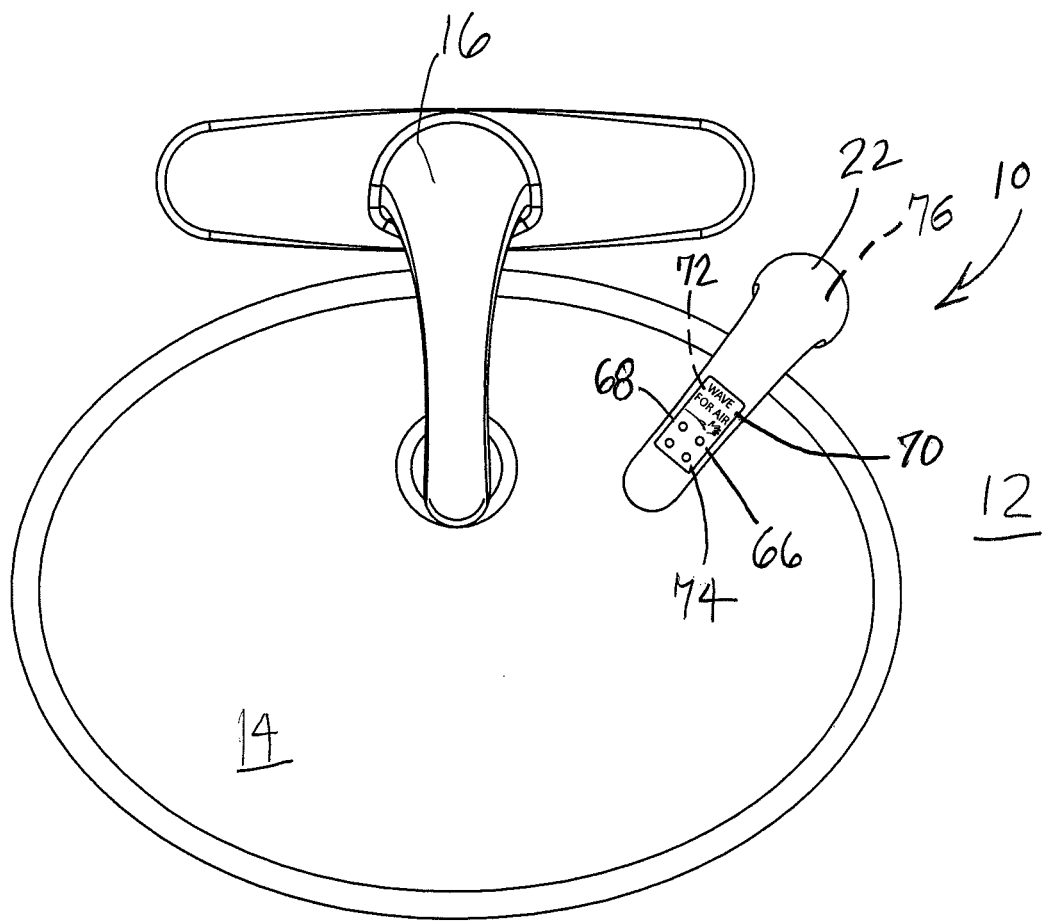
FIG. 11 is a top down view of an embodiment of an air dispensing apparatus with infrared sensors and messaging on the top surface according to the disclosure as a side mount on the counter of a sink.

Referring now to FIG. 11, in embodiments, the spout assembly 22 (shown in a top plan view) can be structured with an infrared sensor 66 positioned in an upward orientation for sensing hand motion above the spout assembly 22. In embodiments, the sensor 66 is an infrared sensor or a capacitance sensor. Such placement of the infrared sensor 66 above the spout advantageously differentiates the required hand movement for activation of the air dispensing system from the sensor of an automatic water faucet, and avoids accidental or premature triggering of air flow from the system while water is being dispensed and hands are being washed. The placement of the infrared sensor 66 above the spout also eliminates extremely narrow object-in-view tolerances due to the varying surfaces and distances of the sink below and the surface light reflection which can cause problems with the operation of downwardly directed IR sensors.

As depicted in FIG. 11, the spout assembly 22 can be structured with a translucent covering 68 with markings or a decal 70, which include a symbol or wording of instruction for operation of the device (e.g., the message "wave for air") with one or more LED indicator lights 72 positioned underneath to flash or otherwise illuminate the overlying symbol or wording. The spout assembly 22 can also be structured to include one or more LED indicator lights 74 positioned underneath the translucent covering 68, being optionally colored, for example, to indicate power, low power, low fragrance and to replace the fragrance dispersing module 56, to indicate low filter and to replace the air filter 54, etc. The infrared sensor 66 and the LED lights 72, 74 are connected via wiring to a processor (PCB) 76 within the spout assembly, which, in turn, is connected to a power source. The processor 76 is configured to communicate with the sensor 66, the LED indicator LED lights 72, 74 and the fan motor 46 via wiring to turn on and off the fan motor 46 of the drying module 28 when the infrared sensor 66 is or isn't activated.

In installing the air dispensing apparatus 10 as a side mount with an automatic faucet 16, water flow can be activated by movement of the hands in proximity to a sensor associated with the water faucet 16, and air flow can then be activated by movement of the hands in proximity to the infrared sensor 66 associated with the air dispensing apparatus 10.

In embodiments, the electronics of the air dispensing apparatus 10 and an automatic faucet 16 can be connected through a processor to synchronize the two systems to function together such that the automatic faucet is first activated and, when the water flow stops, the air dispensing apparatus 10 is then actuated to deliver air to dry the hands.

The processor connected to both systems can also be programmed as to when (and/or for how long) the automatic faucet 16 and/or the air dispensing apparatus 10 are activated, among other configurations.

In cases in which it is desired to install the air dispensing apparatus 10 with an existing faucet, a retrofit can be readily achieved on the side of an already installed faucet (manual or automatic). In embodiments, the air dispensing apparatus 10 can be installed as a side mount in conjunction with an existing manual faucet and, in use, once a subject is done washing their hands, they would simply turn off the faucet and activate the air dispensing apparatus 10 by waving a hand over the spout assembly 22 to actuate the device.

Figure 12:
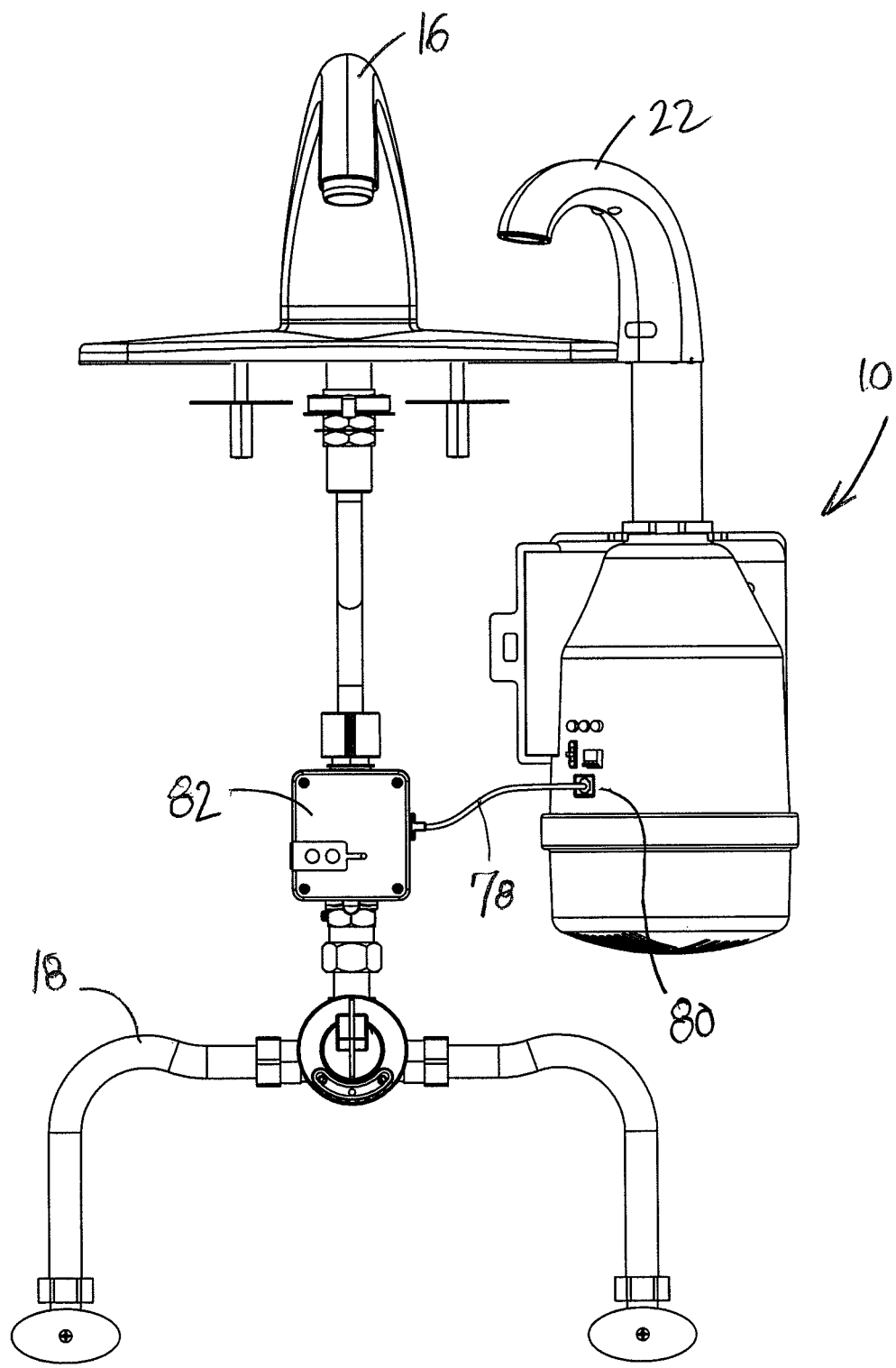
FIG. 12 is a perspective view of an embodiment of a set-up of an air dispensing apparatus according to the disclosure as a side mount on the counter of a sink.

In a side mount arrangement, the positioning of the infrared sensor 66 in the upper surface of the spout apparatus 22 for activation of the air dispensing apparatus 10 substantially avoids accidental triggering of the sensor in the adjacent automatic faucet. Referring now to FIG. 12, in some embodiments in which the side mount installation of the air dispensing apparatus 10 is a retrofit of an existing faucet (manual or automatic), a wire 78 from the electronics 80 of the air dispensing apparatus 10 can be connected to the water intake 82 for the water faucet 16, such that if the water is on and flowing, the air dispensing apparatus 10 will not activate until the water flow stops. This set-up ensures that only one of the systems is working at any one time and/or sequenced such that upon completion of a hand washing, the air would initiate for a set period of time.

Figure 13:
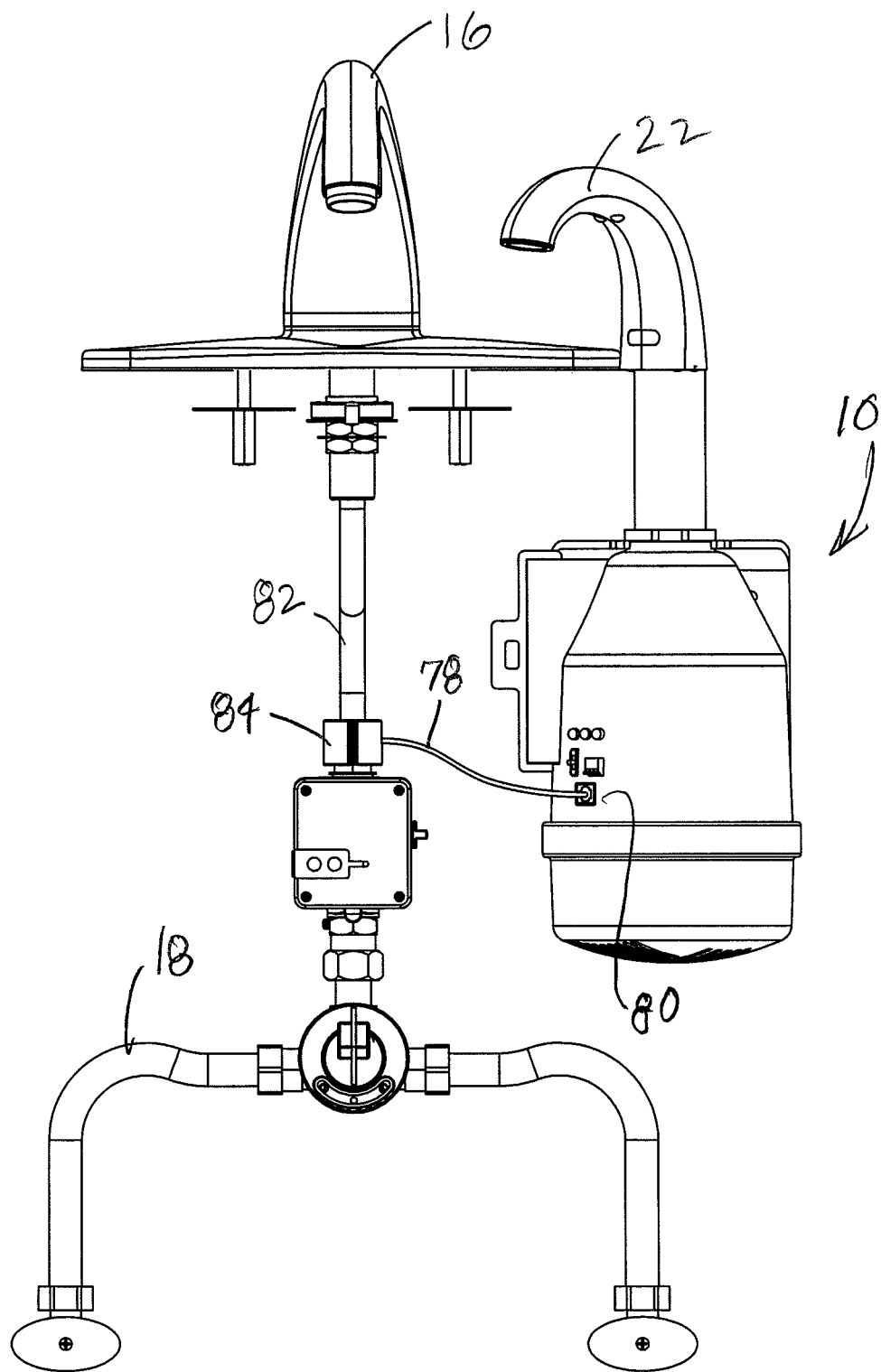
FIG. 13 is a perspective view of another embodiment of a set-up of an air dispensing apparatus according to the disclosure as a side mount on the counter of a sink.

In another embodiment of a retrofit installation, illustrated in FIG. 13, an electro-mechanical valve 84 can be attached to the water intake pipe 82 leading to an installed automatic faucet 16 (just prior to the faucet), and the electro-mechanical valve 84 can be connected to the electronics 80 of the air dispensing apparatus 10, which activates the valve 84 to override and stop water flow to the faucet 16 when the air dispensing apparatus 10 is functioning. In this arrangement, the valve 84 closes the pipe 82 to stop the flow of water to the automatic faucet 16. This set-up can be used in applications in which the sensor associated with the automatic faucet 16 continues to go on when the air dispensing apparatus 10 is activated, or if the faucet 16 employs a capacitance sensor that senses a hand or other object in proximity to the sensor (e.g., in a 360° radius) rather than under a specific focal point (as is typical with an IR sensor), which could repeatedly or continuously turn the faucet on during use of the air dispensing apparatus 10.

The mechanical valve assembly 84 is thus controlled by the air dispensing apparatus 10 such that when the air dispensing apparatus is activated, the associated firmware in the system communicates to the valve to shut off water flow. Then, upon completion of the hand drying, the valve would open and the water would be dispensed. This set-up allows an existing automatic faucet to be retrofitted with the air dispensing apparatus with the need for replacement.

In another embodiment, FIGS. 14-19 illustrate an air dispensing apparatus 86 according to the disclosure, which is structured as a multi-functional system to deliver air and water or other fluid.

Figure 14:
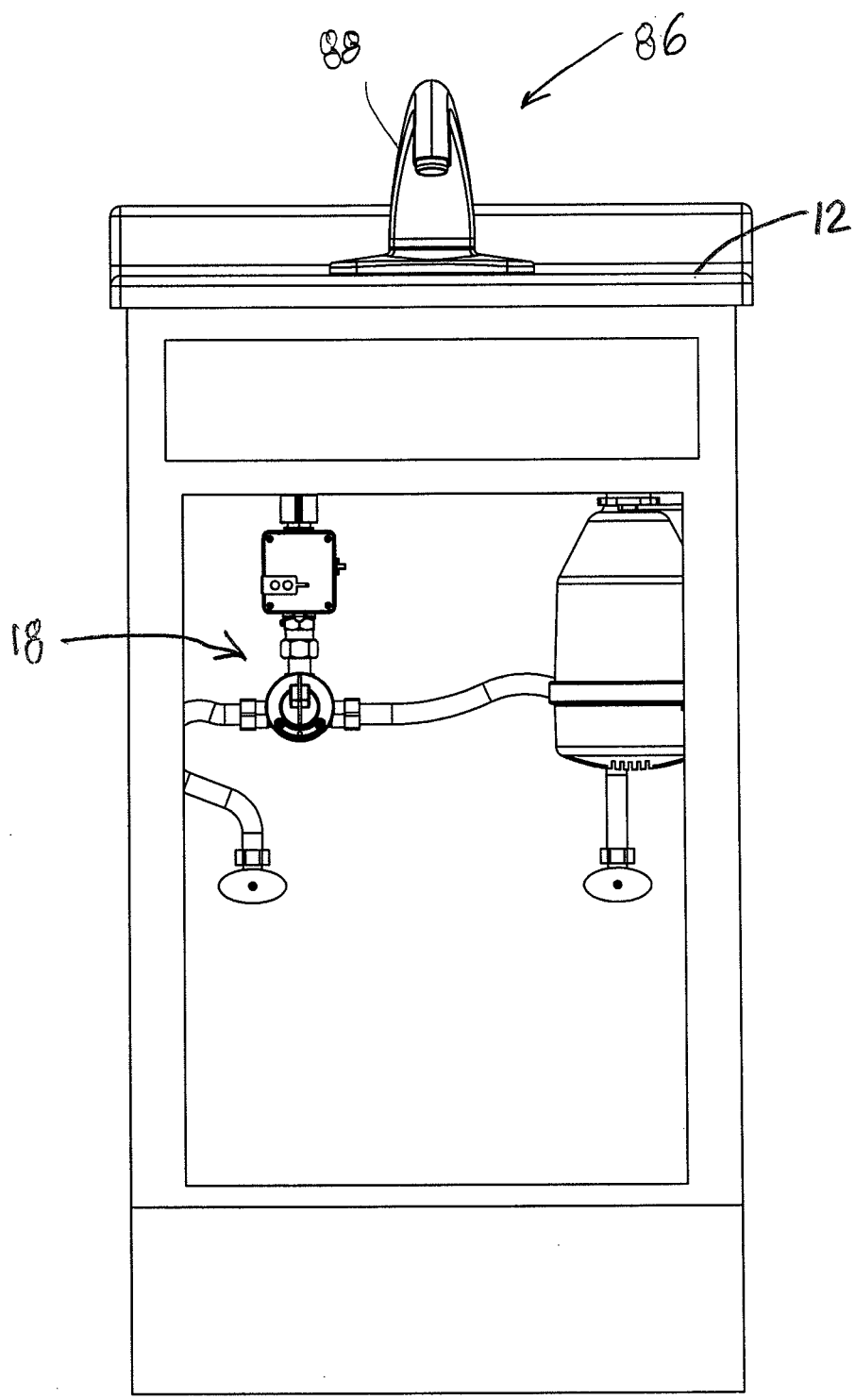
FIG. 14 is a front view of an embodiment of a multi-functional air dispensing apparatus according to the disclosure mounted on the counter of a sink.
Figure 15:
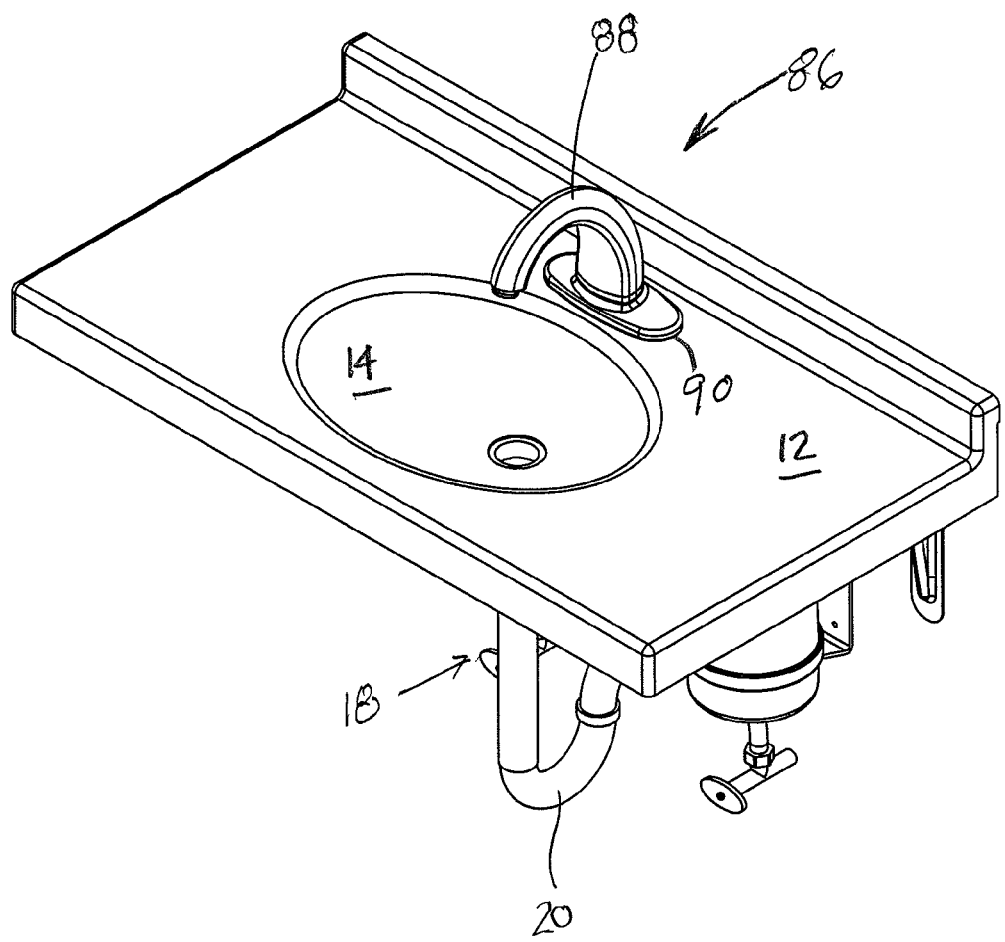
FIG. 15 is a perspective view of the multi-functional air dispensing apparatus of FIG. 14.
Figure 16:
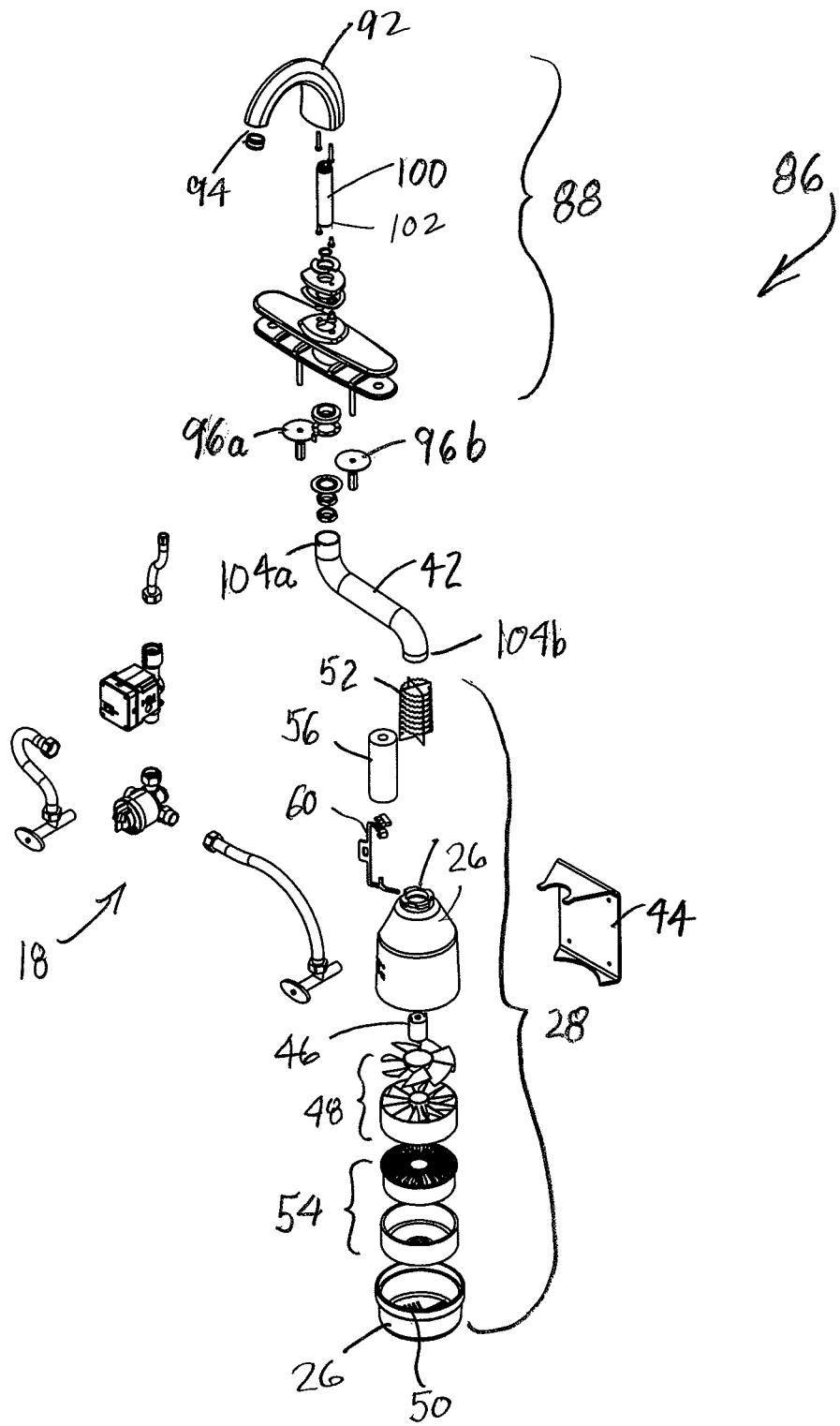
FIG. 16 is an exploded view of the air dispensing apparatus of FIG. 14.
Figure 17:
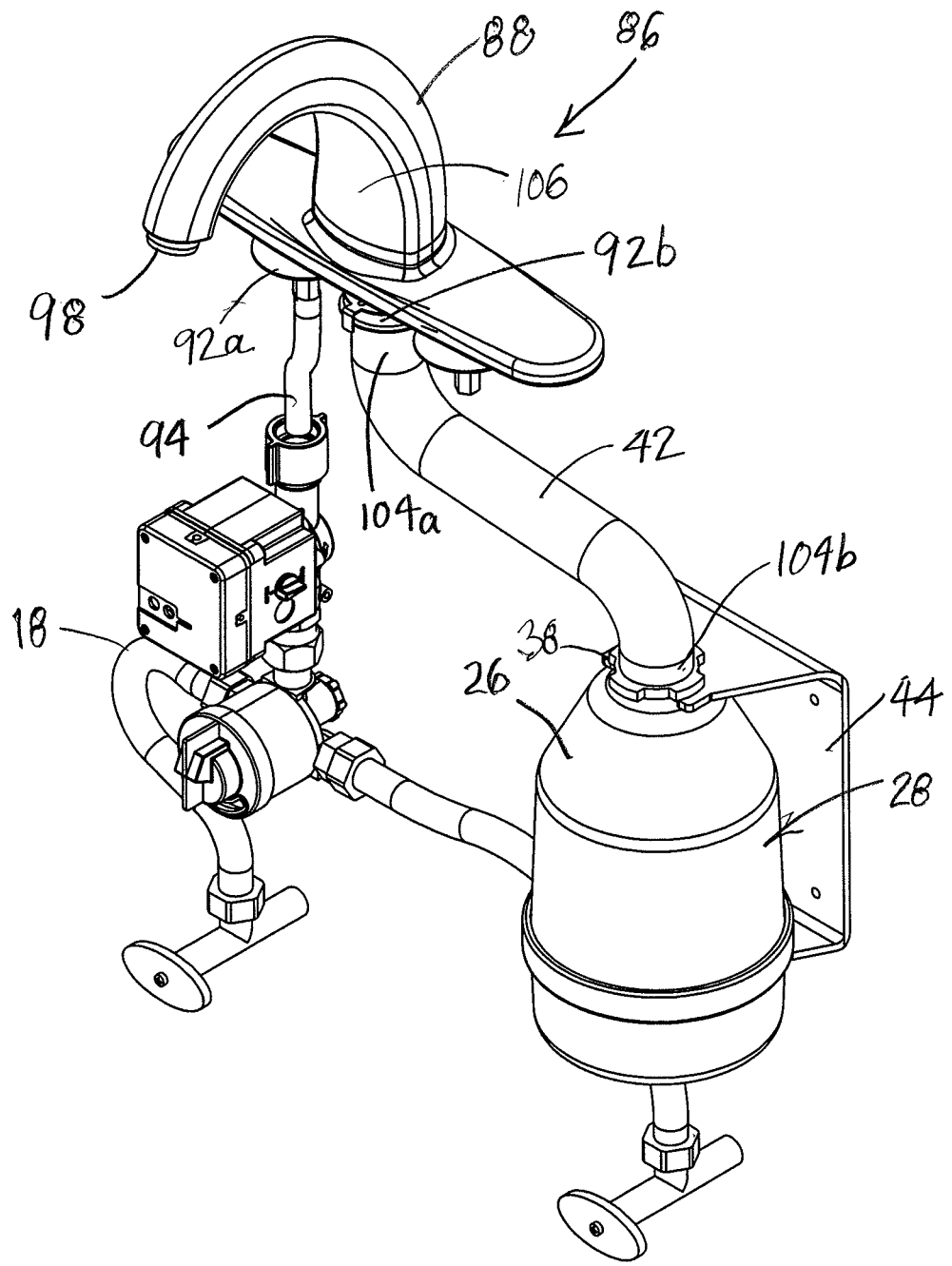
FIG. 17 is a perspective view of the air dispensing apparatus as depicted in FIG. 14, with the sink and counter not depicted.
Figure 18:
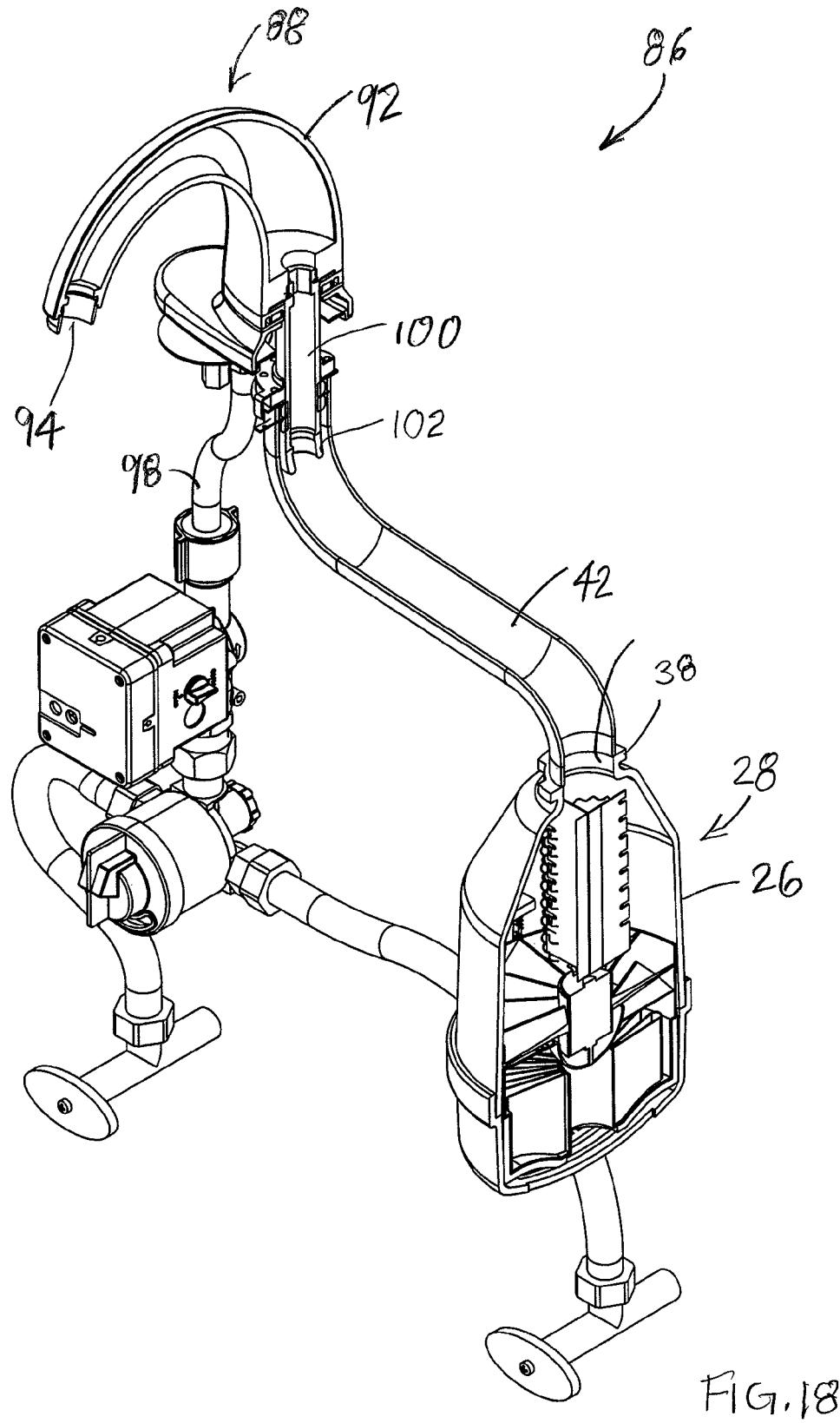
FIG. 18 is an elevational, cross-sectional view of the air dispensing apparatus of FIG. 17.

Referring to FIGS. 14-15, in the depicted embodiment, the multi-functional air dispensing apparatus 86 is shown mounted through a counter 12 of a sink 14 as a center mount. Also depicted are a water valve and mixer assembly 18 for automatic hot and cold water delivery and a standard plumbing drain 20 connected to the sink 14. FIG. 18 illustrates the apparatus 86 in an exploded view, and FIGS. 16-17 depict the air dispensing apparatus 86 without the presence of the counter 12 or sink 14.

As illustrated, the multi-functional air dispensing apparatus 86 comprises a spout assembly 88 mounted through a hole 90 in the counter 12 (or other support substrate). The multi-functional air dispensing apparatus 86 incorporates the air drying module 28 as described hereinabove with respect to the embodiment of the air dispensing apparatus 10 depicted in FIG. 1-8.

The spout assembly 88 is structured with a spout housing 92 having an outlet 94 for dispensing the water and the air therethrough. The spout assembly 88 includes separate connections 96a, 96b to a water source (line) 98 and to the housing 26 of an air drying module 28, which are positioned under the counter 12. The connections 96a, 96b are mounted onto separate openings into the spout housing 92.

In embodiments, the housing 26 of the drying module 28 is releasably connected to the spout assembly 88 via a flexible tubing 42, and the drying module 28 is affixed to a support bracket 44 that can be mounted on a supporting wall or other substrate.

The spout assembly 88 includes a tubular connector 100 having an end 102 that is structured for mating connection onto a first end 104a of the flexible tubing 42. The second end 104b of the flexible tubing 42 is structured for mating connection to the open end 38 of the housing 26 of the drying module 28. In embodiments, the ends 104a, 104b of the flexible tubing 42 are connected to the tubular connector 100 and the housing 26 of the drying module by a quick release mechanism, for example, by a bayonet mount.

Figure 19:
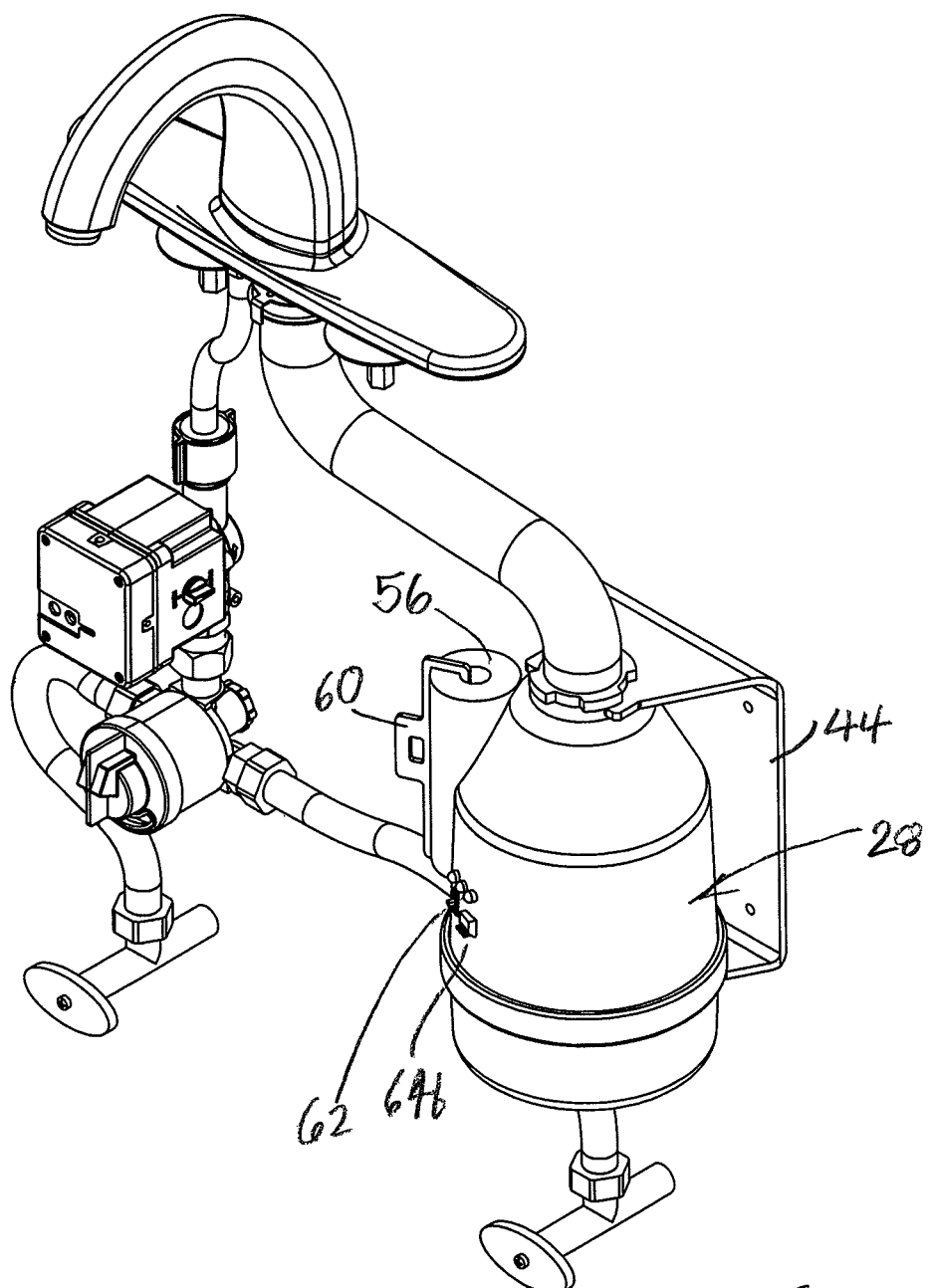
FIG. 19 is an embodiment of a multi-functional air dispensing apparatus according to the disclosure with a fragrance dispersing module mounted thereon.

As illustrated in FIG. 19 (similar to the embodiment of the air dispensing apparatus 10 described hereinabove), the drying module 28 can include LED indicator light(s) 62 and/or control switch(es) 64a, 64b, and a fragrance dispersing module 56.

The air dispensing apparatus 86 further includes one or more sensors which can be positioned below or above the spout assembly 88 as described hereinabove for the embodiments of the air dispensing apparatus 10. For example, FIG. 17 illustrates a sensor 106 situated below the spout assembly 88. In embodiments, the sensor is a capacitance sensor or infrared sensor. For example, the sensor can be a capacitance sensor which is configured to sense hands in a nearby proximity and signal a processor to close a circuit, initiate dispensing of water to wash the hands, end the water flow and initiate air flow from the drying module 28.

In embodiments of the multi-functional air dispensing apparatus, activation of the sensor activates a microprocessor configured to first activate the water source dispenser for a first time period to dispense water through the outlet of the spout assembly, then secondly activate the drying module to draw air into the drying module and force the air through the outlet of the spout assembly for a second time period. In another embodiment, first and second infrared sensors can be positioned on either side of the spout assembly 88, on top of the spout assembly (e.g., as shown in FIG. 11) or below the spout assembly (e.g., as shown in FIG. 17) wherein activation of the first sensor actuates water flow and activation of the second sensor actuates air flow. In other embodiments, a first sensor can be positioned below the spout assembly 88 to sense hand movement to start the water flow (as depicted in FIG. 17 and in FIG. 3 by sensor 66) and a second sensor can be positioned on top of the spout assembly 88 to initiate air flow (as depicted in FIG. 11 by sensor 66). In embodiments, the infrared sensor is programmed through a processor to dispense water by a single pass of an object, and dispense air by two or more passes of an object within a set time period.

It is specifically intended that the present disclosure not be limited to the embodiments and illustrations contained herein, but include modified forms of those embodiments including portions of the embodiments and combinations of elements of different embodiments as come within the scope of the following claim.

We claim:

1. An apparatus for automatically dispensing water and air, comprising:
    a spout assembly mounted through a support substrate, the spout assembly connected to a water source dispenser and to a drying module comprising a housing;
    the spout assembly structured with a single outlet for dispensing the water and the air therethrough, an infrared sensor, one or more indicator lights, and a bottom end comprising first and second openings;
    a first tubular element connecting the first opening to the housing of the drying module, and a second tubular element connecting the second opening to the water source dispenser; and
    the housing of the drying module containing a motor-driven fan operable for forcing airflow through the outlet of the spout assembly, and an air intake vent.

2. The apparatus of claim 1, wherein activation of the infrared sensor activates a microprocessor configured to first activate the water source dispenser for a first time period to dispense water through the outlet of the spout assembly, then secondly activate the drying module to draw air into the drying module and force the air through the outlet of the spout assembly for a second time period.

3. The apparatus of claim 1, comprising first and second infrared sensors, wherein activation of the first sensor actuates water flow and activation of the second sensor actuates air flow.

4. The apparatus of claim 1, wherein the infrared sensor is programmed to dispense water by a single pass of an object, and dispense air by two or more passes of an object within a set time period.

5. The apparatus of claim 1, wherein the housing of the drying module further contains a fragrance dispersing mechanism.

6. The apparatus of claim 1, wherein the housing of the drying module further contains an air heating mechanism.

7. The apparatus of claim 5 wherein the fragrance dispersing mechanism is a fragrance dispersing module either constructed of a fragranced material or containing a fragranced material.

8. The apparatus of claim 1, wherein the first tubular element is connected to the spout assembly and the drying module by a quick release mechanism.

9. The apparatus of claim 1, wherein the drying module is affixed to a wall bracket.

10. The apparatus of claim 1, wherein the drying module further comprises an air filter.

11. The apparatus of claim 1, wherein the drying module further comprises a switch.

12. The apparatus of claim 6, wherein the drying module is configured with an on/off switch to the air heating mechanism.

13. The apparatus of claim 1, wherein the drying module further comprises a fragrance module containing a fragrance material.

14. The apparatus of claim 13, wherein the fragrance module comprises a housing containing the fragrance material, the housing configured with air vents for passage of air therethrough from the drying module by activation of the drying module, wherein the fragrance is dispersed into the air outside the drying module and does not pass into the spout assembly.

15. The apparatus of claim 14, wherein the housing of the fragrance module comprises a fragranced material.

16. The apparatus of claim 14, wherein the housing of the fragrance module contains a wicking material comprising a fragrance substance.

17. The apparatus of claim 13, the fragrance module is releasably mounted in an external structure of the drying module.

18. The apparatus of claim 16, wherein the fragrance module comprises a handle.

19. The apparatus of claim 13, wherein the drying module or the fragrance module is configured with a mechanism to control air flow from the drying module into the fragrance module.

20. The apparatus of claim 1, wherein the support substrate comprises a sink, a counter of a sink, a table, or a cabinet.

* * * * *